United States Patent [19]

Carmen et al.

[11] Patent Number: 4,609,372

[45] Date of Patent: Sep. 2, 1986

[54] HEAT STERILIZABLE STORAGE SOLUTION FOR RED BLOOD CELLS

[75] Inventors: Raleigh A. Carmen, Concord; Chiyong Chong, San Francisco; Barry Leng, Pleasant Hill, all of Calif.

[73] Assignee: Miles Laboratories, Inc., Elkhart, Ind.

[21] Appl. No.: 541,813

[22] Filed: Oct. 13, 1983

[51] Int. Cl.[4] ............................................. A61B 13/16
[52] U.S. Cl. .................................. 604/262; 604/410; 424/101
[58] Field of Search ................. 424/101; 604/262, 410

[56] References Cited

U.S. PATENT DOCUMENTS

| | | | |
|---|---|---|---|
| 3,874,384 | 4/1975 | Deindoerfer et al. | 424/101 |
| 4,195,632 | 4/1980 | Parker et al. | 604/411 |
| 4,435,179 | 3/1984 | Walker | 604/410 |

Primary Examiner—John Kight
Assistant Examiner—Kriellion Morgan
Attorney, Agent, or Firm—James A. Giblin

[57] ABSTRACT

Aqueous storage solution for red blood cells comprising a stabilized ascorbate derivative and having a pH sufficient to maintain substantially all of the initial concentration of ascorbate derivative and avoid formation of ascorbate degradation products during heat sterilization. A preferred solution includes at least about 90% of the pre-sterilization ascorbate and adenine but is free of dextrose.

15 Claims, 2 Drawing Figures

HEAT STERILIZABLE STORAGE SOLUTION FOR RED BLOOD CELLS

SPECIFICATION BACKGROUND OF THE INVENTION

1. Field of the Invention

This invention is concerned generally with the maintenance of 2,3-diphosphoglycerate levels of red blood cells during extended storage, and specifically and a heat-sterilizable solution for achieving such storage.

2. Description of the Prior Art

Human blood is typically collected and processed using so-called multiple blood bags consisting of a medical grade plastic primary bag (for collecting whole blood from a blood donor) connected to one or more secondary bags into which various components of blood may be expressed for storage and later use. Examples of such multiple blood bags are shown in U.S. Pat. No. 3,064,647 to Earl and U.S. Pat. No. 4,195,632 to Parker et al. The introduction of multiple blood bag systems for blood collection and processing has made it possible for blood banks to supply an increasing range of blood components for transfusion. As a consequence, the processing of blood into components has increased dramatically. Because of this attention is being directed to methods of enhancing the storage properties of such components.

The first component removed from whole blood is platelet-rich plasma. This is obtained conventionally by centrifugation to separate the plasma and packed red cells. Such red cell preparations are replacing whole blood to an increasing extent in blood transfusion therapy. When plasma is removed from whole blood leaving a red cell concentrate, the increased viscosity of the concentrate makes rapid transfusion difficult and, accordingly, requires dilution (e.g., with a physiological saline solution) to flow properly. In addition, red blood cell concentrates lose glucose and adenine, and as a result, maintenance of a sufficient red blood cell ATP level may be difficult. Also, it is desirable to maintain the 2,3-diphosphoglycerate (2,3-DPG) level of red blood cells leading to improved red blood cell oxygen offloading characteristics.

When whole blood is drawn from a donor, it is commonly collected into a plastic blood bag containing an anticoagulant or preservative solution such as acid-citrate-dextrose (ACD), USP XX, page 49; citrate-phosphate-dextrose (CPD), USP XX, pages 49–50, CP2D which contains twice the amount of dextrose as CPD, Lovric et al, *Med. J. Aust.*, 1977, 2, 183–186; or CPD plus adenine (CPDA or CPDA-1), Zuck et al, Transfusion, 17, 374–382 (1977). All of the above references are incorporated herein by reference. Whole blood collected into ACD or CPD can be stored for 21 days under conventional blood banking procedures, and red cell concentrates stored in ACD or CPD also remain viable for 21 days. The storage life of whole blood has been extended to about 35 days with CPDA-1 as the anticoagulant or preservative solution. However, storage of red cell concentrates for extended periods in CPDA is marginal (see Zuck et al, ibid.).

As mentioned above, dilution with a physiological saline solution has been used to enhance the flow properties of red cell concentrates. This introduces an extra handling step for clinicians, since the dilution step generally must be carried out shortly before infusion.

In attempting to overcome the above difficulties it has been reported by Lovric et al, *The Medical Journal of Australia*, 1977, 2, 183–186 that red blood cell concentrates may be stored for 35 days when mixed with an adenine-enhanced electrolyte solution containing trisodium citrate, citric acid, disodium hydrogen phosphate, dextrose, sodium chloride, and adenine. Högman et al in Transfusion, 18, 233–241, 1978, and Högman et al, The New England Journal of Medicine, 299, 1337–1382, 1978, reported the dilution of red blood cells, prepared from whole blood conventionally collected into a CPD-medium, with saline-adenine-glucose (SAG). The red cell concentrate mixed with SAG can be stored for a period of up to 35 days.

U.S. Pat. No. 4,267,269 discloses a storage solution for packed red cells which contains SAG plus mannitol. The solution contains, per 100 ml, 5–50 mg of adenine, 1000–3500 mg of glucose or fructose, 400–1200 mg of sodium chloride, and 250–2000 mg of mannitol.

Storage solutions for red cell concentrates containing dextrose, sodium dihydrogen phosphate, and mannitol with or without inosine and adenine are taught by Ginzburg in Bibl. Haemat., No. 38, part II, pp 217–220, 1971. Beutler ("The Red Cell in Vitro", Grum and Stratton, New York, N.Y., 189–216, 1974) and Wood et al (Blood, 42, 17–25, 1973) describe a red cell storage medium comprising sodium bicarbonate, sodium carbonate, sodium phosphate, adenine, glucose, and mannitol.

It is known that CPD adenine supplemented with sodium ascorbate and dihydroxyacetone improved maintenance of red cell 2,3-DPG during prolonged storage (Wood et al, Transfusion, 14, 272, 1974). Unfortunately, however, sodium ascorbate and ascorbic acid are unstable in aqueous solution. A stabilized derivative of ascorbic acid, ascorbate phosphate, has been evaluated in conjunction with dihydroxyacetone and CPD-adenine (Bensinger et al, Transfusion, 16, 518, 1976). It was shown, however, that ascorbate phosphate in aqueous solution at pH 5–8 was s degraded to an extent of about 25% upon autoclaving the solution at 121° C. for 20 minutes. See the Bensinger et al article cited above. Moore et al, in Transfusion, 21, 723–731, 1981, have disclosed optional additive solutions. CPD-collected red blood cells in a solution containing adenine, glucose, and ascorbate phosphate or CPD-adenine collected red blood cells in a solution containing ascorbate phosphate have each indicated the potential to store red blood cells at least 42 days and to maintain red blood cell 2,3-DPG.

Unfortunately, however, the degradation of ascorbate phosphate during autoclaving or heat sterilization presents a substantial disadvantage to the use of ascorbate phosphate to maintain red blood cell 2,3-DPG. Such degradation not only reduces the effective amount of ascorbate phosphate but also results in degradation products which may be toxic.

SUMMARY OF THE INVENTION

The degradation of a stabilized ascorbate derivative such as ascorbate phosphate in aqueous solutions during heat sterilization can be minimized by maintaining the solution at a high pH, preferably a pH of 8.0 or higher. One preferred embodiment of the invention is an aqueous solution for storage of red blood cells which comprises a stabilized ascorbate derivative and a purine base (such as adenine), the solution having a pH sufficient to maintain the amount of ascorbate derivative (in an undegraded form) at a level of ninety percent or more by weight during heat sterilization of the composition. In a very preferred embodiment, the solution is substantially free of a red blood cell nutrient sugar such as dextrose to avoid discoloration which occurs when aqueous solutions of sugars are heat sterilized at a high pH.

Another embodiment of the invention is a heat sterilizable combination comprising a plastic blood bag containing an aqueous red cell storage solution comprising a stabilized ascorbate derivative and having a pH sufficient to maintain the amount of undegraded ascorbate derivative at a level of ninety percent or more by weight during heat sterilization of the combination.

Another embodiment of the invention is a multiple blood bag system comprising a donor bag for receiving blood from a donor pre-connected to the heat sterilizable combination described in the preceding paragraph.

DESCRIPTION OF THE PREFERRED EMBODIMENTS

Figure 1:
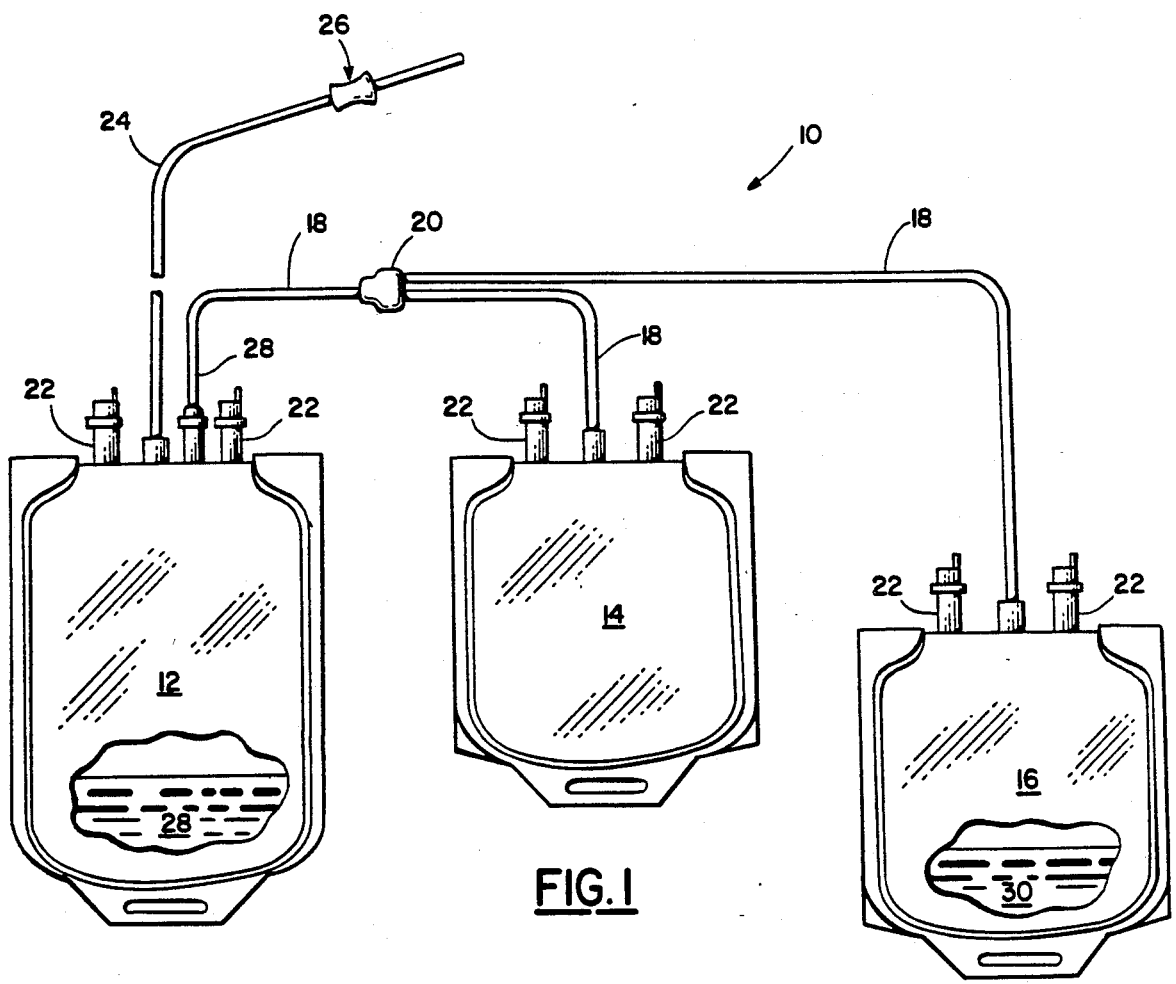
FIG. 1 illustrates pre-connected multiple blood bags, one of which contains the buffered storage solution of this disclosure.

As used herein, the maintenance of substantially all of the initial ascorbate derivative level during and after heat sterilization means that at least about 90% percent by weight of the initial ascorbate level remains. Heat sterilization means subjecting the products of this invention to a temperature of at least about 114° C. for at least about 30 minutes.

As mentioned above, one embodiment of the invention is a solution for storage of red blood cells which is substantially free of a red blood cell nutrient source such as dextrose. The solution comprises a stabilized ascorbate derivative, adenine, and has a pH sufficient to maintain the amount of undegraded ascorbate derivative at a level of ninety percent or more by weight during heat sterilization of the solution. The term red blood cell nutrient source means a material that will provide a source of energy for the red blood cells such as a sugar, for example, dextrose (glucose). Other such nutrient sources are fructose, mannose, and galactose. The composition is substantially free of such nutrient source if it contains less than about 0.01 percent thereof, preferably, less than about 0.001 percent.

The term stabilized ascorbate derivative means a derivative of ascorbic acid, such as ascorbate-2-phosphate, ascorbate-3-phosphate, ascorbate 2,2' phosphate, and the like, which is stable to heat sterilization.

As the ascorbate phosphate one may use, by way of example and not limitation, metallic salts of ascorbate-2-phosphate such as trisodium ascorbate-2-phosphate, tripotassium ascorbate-2-phosphate, and the like. The pH sufficient to maintain the concentration of undegraded ascorbate derivative at a level of ninety percent or more during heat sterilization is generally greater than about 8, preferably about 8.5–9.5. Pre-sterilization pH can be obtained with an alkaline form of the ascorbate derivative itself and/or the use of an appropriate buffer (e.g. phosphate buffers such as di or tri sodium phosphate). The buffer prevents pH fall that would otherwise occur during heat sterilization.

A typical heat sterilizable red cell storage solution of this invention is an aqueous solution containing, per 100 ml of solution, 200–600 mg of ascorbate phosphate and 5–50 mg of adenine at a pH greater than about 8. Preferably, the heat sterilizable red cell storage composition of the invention is an aqueous solution containing, per 100 ml of solution, 20–45 mg of adenine and 350–450 mg of ascorbate phosphate at a pH of about 8.5–9.5. Such solution is preferably substantially free from a red blood cell nutrient source (such as carbohydrates) and, when heat sterilized, should maintain a level of undegraded ascorbate phosphate of about 90% by weight or more.

Usually about 75–100 ml of the aforementioned heat sterilizable red cell storage composition are mixed with 225–250 ml of a red cell concentrate to achieve the maintenance of 2,3-DPG during extended storage of the red blood cell concentrate.

Another embodiment of the invention is a heat sterilizable combination comprising a flexible, plastic blood bag containing a red cell storage solution comprising a stabilized ascorbate derivative and having a pH sufficient to maintain the amount of undegraded ascorbate derivative at a level of ninety percent or more by weight during heat sterilization of the combination.

The above-described combination preferably includes a purine base such as adenine in an amount of 5 to 50 mg, preferably 20–45 mg.

The above-described heat sterilizable solution may be used individually. For example, the combination may be heat sterilized and then connected to a blood bag containing red blood cells by means of a sterile connector such as that disclosed in U.S. Pat. No. 4,022,256.

The aforementioned heat sterilizable combination may also be interconnected to a multiple blood bag system as shown in FIG. 1. The system of FIG. 1 shows a donor bag 12 for receiving blood from a donor and one or more satellite bags 14 and 16, communicating by flexible tubing 18 and conventional Y connector 20 with the donor bag, for receiving a blood component such as a red cell concentrate or a platelet concentrate from the donor bag. One of the satellite bags (16) is the above-mentioned heat sterilizable combination. Both donor bag 12 and satellite bags 14 and 16 are equipped with hermetically sealed access ports 22, and bag 12 further has a blood collection tube 24 to the outer end of which is secured a donor needle assembly 26. Usually, the donor bag 12 will contain an anticoagulant such as CPD, CPD plus adenine, CP2D, or the like. The entire blood bag system is heat sterilized and packaged. In use, blood is drawn from a donor using needle 26 into donor bag 12 in which the blood mixes with anticoagulant 28. The blood is treated to separate plasma from a red cell concentrate usually by centrifugation. The plasma is expressed into satellite bag 14 and tubing 18 is sealed above bag 14 and severed from the system. The storage solution 30 in heat sterilizable combination represented by 16 is expressed through tubing 18 into bag 12 wherein the storage solution mixes with the packed red cells. Tubing 18 is sealed above bag 12 and severed. Generally, red cell concentrates are stored at a temperature of about 4° C. until used. The concentrates after mixture with the present red cell storage composition may be stored for at least 21 days, usually at least 35 days, with maintenance of 2,3-DPG at levels comparable with fresh red blood cell concentrates for up to 28 days. Generally, such stored red blood cells should also exhibit clinically acceptable levels of hemolysis, adenosine triphosphate (ATP), and osmotic fragility obtainable by methods known in the art.

Figure 2:
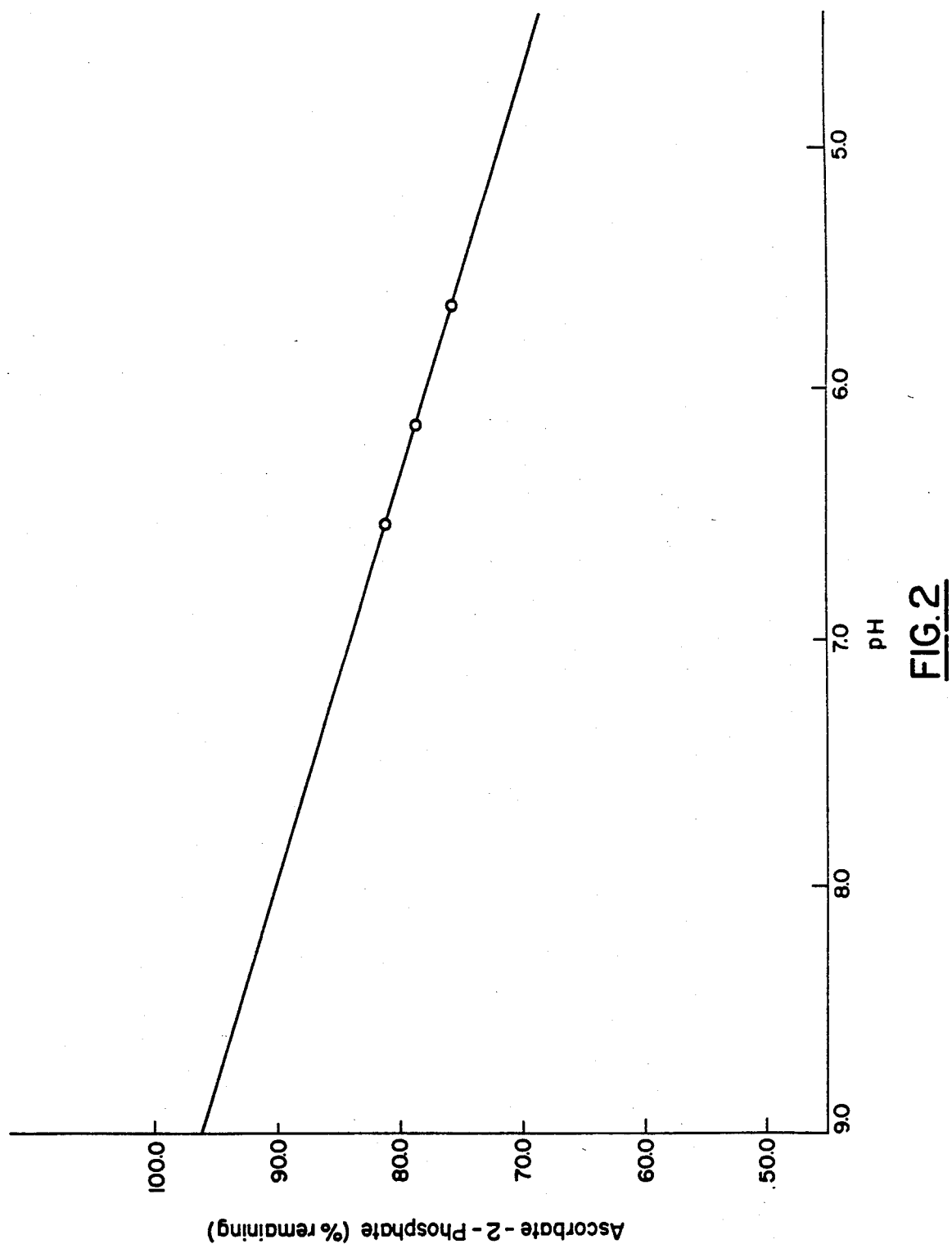
FIG. 2 is a graph showing the effects of pH change on ascorbate-2-phosphate stability.

FIG. 2 is a graph showing the reduction of ascorbate-2-phosphate (% of initial value) as a function of pH.

EXAMPLES

The invention is demonstrated further by the following illustrative examples.

EXAMPLE 1

An additive solution was formulated and had the following composition:

TABLE I

|  | Grams/Liter |
| --- | --- |
| Sodium Chloride, U.S.P. | 8.50 |
| Adenine | 0.227 |
| Sodium Phosphate Anhydrous, Dibasic, U.S.P. | 1.144 |
| Trisodium-L-Ascorbate-2-Phosphate (Miles Laboratories, Inc.) | 3.97 |
| pH | 9.0 |

An aliquot of the above formulation was heated at 114.5° C. for a period of 55.5 minutes. After heating, the aliquot was analyzed for degradation of the ascorbate phosphate by HPLC utilizing an anion exchange column. In addition, color development was assessed by measuring $A_{4.0\ cm}^{375\ nm}$. The results indicated that 90.0% of the ascorbate phosphate remained undegraded after heating and the $A_{4.0\ cm}^{375\ nm}$ was 0.348.

For purposes of comparison a similar experiment was done on an additive solution having the following composition:

TABLE II

|  | Grams/Liter |
| --- | --- |
| Sodium Chloride | 7.0 |
| Glucose | 10.0 |
| Adenine | 0.227 |
| Trisodium-L-Ascorbate-2-Phosphate | 3.97 |
| Sodium Phosphate Monobasic | 2.00 |
| pH | 6.8 |

The results indicated that only 76% of the ascorbate phosphate remained after heating and the $A_{4.0\ cm}^{375\ mm}$ was 2.444.

EXAMPLE 2

The 2,3-diphosphoglycerate concentration of red cells stored in the presence of the additive solution of the invention was studied.

Six units of whole blood were drawn into a conventional DEHP-PVC donor blood bag. The anticoagulant in the donor bag was 63 ml of CP2D. The hematocrit was adjusted to 85% and plasma was separated from the red cells.

An additive solution was prepared and had the following composition:

TABLE III

|  | Grams/Liter |
| --- | --- |
| Sodium Chloride | 8.50 |
| Adenine | 0.227 |
| Sodium Phosphate, Dibasic | 1.144 |
| Trisodium-L-Ascorbate-2-Phosphate | 3.97 |

To all units of the packed red cells was added 1 part of the above additive solution to about 3 parts packed red cells, i.e., 75 ml of the additive solution per 230 ml of packed red cells.

The so-treated packed red cells were stored at 4° C. for a period of 6 weeks. Samples were taken at 1-week intervals and examined for 2,3-DPG by the method of Grisolia et al, Anal. Biochem. 31, 235–245 (1969).

The data are summarized in Table IV, along with historical data on red cells preserved with two prior art systems: (1) the CPDA-1, and (2) the Lovric systems described above.

TABLE IV

| | 2,3 DPG, μM/gm Hb | | |
| --- | --- | --- | --- |
| Weeks | Ascorbate System | Prior Art System (1) | Prior Art System (2) |
| 0 | 14.3 | 13.8 | 13.6 |
| 1 | 14.6 | 11.6 | 12.4 |
| 2 | 16.7 | 5.8 | 5.7 |
| 3 | 18.7 | 2.2 | 2.2 |
| 4 | 13.6 | 1.3 | 1.3 |
| 5 | 10.3 | 1.1 | 1.1 |
| 6 | 6.7 | Not Run | 1.1 |

With currently available preservative systems, 2,3 DPG levels are less than 50% of initial value after two weeks storage. The ascorbate system disclosed herein maintains 2,3 DPG at 70% of initial value after five weeks.

Given the above disclosure, it is thought numerous variations will occur to those skilled in the art. Accordingly, it is intended that the scope of this invention should be limited only by the following claims.

What is claimed is:

1. A heat sterilized aqueous solution for storage of red blood cells comprising a stabilized ascorbate derivative, the solution having a pH greater than about 8.0 and sufficient to maintain substantially all of the initial amount of ascorbate derivative during heat sterilization of the composition.

2. The solution of claim 1 wherein the amount of ascorbate derivative is at least about 90% of its pre-heat sterilization amount.

3. The solution of claim 1, wherein the stabilized ascorbate derivative is an ascorbate phosphate.

4. The solution of claim 3 wherein the ascorbate derivative is selected from the group consisting of ascorbate-2-phosphate, ascorbate-3-phosphate and ascorbate 2,2' phosphate.

5. The solution of claim 1 wherein the solution includes adenine.

6. The solution of claim 1 wherein the solution includes inorganic phosphate.

7. The solution of claim 1 wherein substantially all of the initial amount of ascorbate derivative is maintained after heat sterilization at at least about 114° C. for at least about 30 minutes.

8. A multiple blood bag system comprising a donor bag for receiving blood from a donor and a satellite blood bag connected via tubing to the donor bag and containing an aqueous solution of a stabilized ascorbate derivative having a pH greater than about 8.0 and sufficient to maintain the amount of ascorbate derivative at a level of about 90% or more by weight during heat sterilization of the solution.

9. The multiple blood bag system of claim 8 wherein said donor bag contains an anticoagulant.

10. The combination of claim 8 wherein the pH of the red cell storage composition is about 8.5–9.5.

11. The multiple blood bag system of claim 8 wherein the solution is substantially free of a sugar.

12. The multiple blood bag system of claim 8 wherein the stabilized ascorbate derivative is ascorbate phosphate.

13. The multiple blood bag system of claim 12 wherein the ascorbate derivative is selected from the group consisting of ascorbate-2-phosphate, ascorbate-3-phosphate and ascorbate 2,2' phosphate.

14. The multiple blood bag system of claim 8 wherein the solution includes adenine.

15. A multiple blood bag system, as claimed in claim 8, wherein the ascorbate derivative level is maintained after heat sterilization at at least about 114° C. for at least about 30 minutes.

* * * * *